US010098978B2

(12) United States Patent
Saleh et al.

(10) Patent No.: US 10,098,978 B2
(45) Date of Patent: Oct. 16, 2018

(54) WEARABLE CHEMICAL DISPENSER

(71) Applicant: S. C. Johnson & Son, Inc., Racine, WI (US)

(72) Inventors: Saleh A. Saleh, Vernon Hills, IL (US); David C. Belongia, Burlington, WI (US); Nitin Sharma, Kenosha, WI (US); Paul E. Furner, Racine, WI (US); Kwamena Gyakye degraft-Johnson, Racine, WI (US); Raymund J. Alfaro, Oak Creek, WI (US); Donald J. Schumacher, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 15/155,981

(22) Filed: May 16, 2016

(65) Prior Publication Data

US 2016/0256588 A1 Sep. 8, 2016

Related U.S. Application Data

(62) Division of application No. 12/541,328, filed on Aug. 14, 2009, now Pat. No. 9,364,574.

(51) Int. Cl.
*A61L 9/12* (2006.01)
*A01M 1/20* (2006.01)
(Continued)

(52) U.S. Cl.
CPC ........... *A61L 9/122* (2013.01); *A01M 1/2033* (2013.01); *A01M 1/2055* (2013.01);
(Continued)

(58) Field of Classification Search
None
See application file for complete search history.

(56) References Cited

U.S. PATENT DOCUMENTS

| 4,062,649 A | 12/1977 | Kuderna et al. |
| 4,293,095 A | 10/1981 | Hamilton et al. |

(Continued)

FOREIGN PATENT DOCUMENTS

| EP | 0227167 A1 | 7/1987 |
| EP | 1356728 A1 | 10/2003 |

(Continued)

OTHER PUBLICATIONS

Machine-generated English translation of JP 2009-27930, Feb. 12, 2009, pp. 1-10.*

(Continued)

*Primary Examiner* — Kathryn Wright (57) ABSTRACT

Wearable devices for dispensing insect repellents, fragrances, and/or other chemicals along the outside of the clothing of a human are disclosed. They are of the type that are clipped onto a belt or the like, and use a powered fan to dispense active. They are configured with fan rotor arrangements to minimize power use while still achieving acceptable air flow rates. These changes permit use of smaller batteries and more compact arrangements for battery positioning. This in turn permits a much more compact and lightweight construction to achieve the desired results. The devices are also provided with a rotatable clip structure to render use of the device more comfortable when the user is seated and to provide greater control over the direction of the dispensing. Further, they are provided with modified lids to facilitate active refill replacement.

8 Claims, 9 Drawing Sheets

(51) Int. Cl.
*A01M 29/12* (2011.01)
*A61L 9/03* (2006.01)

(52) U.S. Cl.
CPC ............ *A01M 29/12* (2013.01); *A61L 9/032* (2013.01); *A61L 2209/133* (2013.01); *A61L 2209/15* (2013.01)

(56) References Cited

U.S. PATENT DOCUMENTS

| | | |
|---|---|---|
| 4,824,827 A | 4/1989 | Kelly et al. |
| 5,293,648 A | 3/1994 | Finley |
| 5,478,505 A * | 12/1995 | McElfresh .......... B60H 3/0007 239/57 |
| 6,371,450 B1 | 4/2002 | Davis et al. |
| 6,582,714 B1 | 6/2003 | Emmrich et al. |
| 6,926,902 B2 | 8/2005 | Inoue et al. |
| 7,007,861 B2 | 3/2006 | Ketcha et al. |
| 7,152,809 B2 | 12/2006 | Ketcha et al. |
| 7,168,630 B1 | 1/2007 | Ketcha et al. |
| 7,175,815 B2 | 2/2007 | Yamasaki et al. |
| 7,833,492 B2 | 11/2010 | Schumacher et al. |
| 2003/0044326 A1 | 3/2003 | Yamasaki et al. |
| 2003/0160062 A1 | 8/2003 | Inoue et al. |
| 2003/0175171 A1 | 9/2003 | Yamamoto et al. |
| 2005/0079113 A1 | 4/2005 | Selander |
| 2006/0039835 A1 | 2/2006 | Nottingham et al. |
| 2006/0043619 A1 | 3/2006 | Brown et al. |
| 2006/0137241 A1 | 6/2006 | Yamasaki et al. |
| 2007/0036688 A1 | 2/2007 | Hayes-Pankhurst et al. |
| 2007/0183940 A1 | 8/2007 | Yamamoto et al. |
| 2008/0141928 A1 | 6/2008 | Adair et al. |
| 2009/0008411 A1 | 1/2009 | Schumacher et al. |
| 2009/0060799 A1 | 3/2009 | Torres |
| 2009/0072045 A1 * | 3/2009 | Wheatley .................. A61L 9/03 239/56 |
| 2011/0038761 A1 | 2/2011 | Saleh et al. |

FOREIGN PATENT DOCUMENTS

| | | |
|---|---|---|
| EP | 1698228 A1 | 9/2006 |
| ES | 1063655 | 11/2006 |
| GB | 878040 | 9/1961 |
| GB | 1475004 | 6/1977 |
| JP | 2006505332 A | 2/2006 |
| JP | 2009-27930 A * | 2/2009 |
| JP | 200927930 A * | 2/2009 |
| WO | WO-9632843 A2 | 10/1996 |
| WO | WO-2004043565 A2 | 5/2004 |
| WO | WO-2008034049 A1 | 3/2008 |
| WO | 2009005833 A2 | 1/2009 |

OTHER PUBLICATIONS

PCT/US2008/008289 International Search Report and Written Opinion dated Jan. 14, 2009.

PCT/US2010/002242 International Search Report dated Feb. 25, 2011.

* cited by examiner

WEARABLE CHEMICAL DISPENSER

CROSS-REFERENCES TO RELATED APPLICATIONS

This application is a divisional application of U.S. patent application Ser. No. 12/541,328, filed Aug. 14, 2009.

STATEMENT REGARDING FEDERALLY SPONSORED RESEARCH

Not Applicable.

BACKGROUND OF THE INVENTION

The present invention relates to wearable devices that dispense chemicals such as insect repellents and/or fragrances.

Various techniques have been developed to provide humans with protection from insect bites. For insect control inside buildings a primary emphasis is placed on trying to keep insects from entering the building at all (e.g. placing screens over windows). This sometimes is supplemented with chemical treatment of room air and/or the use of traps. See e.g. U.S. Pat. Nos. 6,582,714 and 7,175,815, and also U.S. Patent Application Publication Nos. 2005/0079113, 2006/0039835, 2006/0137241 and 2007/0036688.

When the individual is outdoors where the area cannot be effectively screened, and the individual is mostly staying in a particular area (e.g. at a picnic, or on a patio near a building), traps and area-repellents are the primary focus.

Alternatively, when the individual is moving away from a single area that they control, individuals often apply a personal insect repellent to clothing or directly to their skin. However, some consumers have expressed a reluctance to apply insect repellents directly to their skin or to delicate clothing.

As a result, portable electrical devices having a fan and an insecticide source have been developed. These devices may have a clip so that they can easily be mounted on a belt, a purse, or even a pocket, and thus be "worn" by the consumer as they move outside. The device may draw air through, or blow air past, a substrate impregnated with an insect repellent or other air treatment chemical, thereby dispensing the active into the air, preferably (in the case of a repellent) downward along the outside of a human's clothing. See, for example, U.S. Pat. Nos. 6,926,902, 7,007,861, 7,152,809, and 7,168,630, and U.S. Patent Application Publication Nos. 2003/0044326, 2003/0175171, 2007/0183940, and 2009/0060799 (also ES 1063655).

However, some such devices may blow the active too far out away from the human body, causing too little of the active to reach locations of primary concern (e.g. near ankles). Other such devices do not provide a way of minimizing waste of the active, such as while blower operation is suspended, between uses. Still other such devices are unduly costly, are too heavy, or have other deficiencies.

The deficiencies in the above noted devices have been addressed by the wearable chemical dispensers described in U.S. Patent Application Publication Nos. 2008/0141928 and 2009/0008411. However, it is still desirable to improve this type of product further, particularly with respect to making the device even more compact and lightweight, making the device easier to use when the consumer is seated, and making the refill unit for the air treatment chemical easier to replace when used up.

Hence, a need still exists to improve devices of this type in these areas.

SUMMARY OF THE INVENTION

In one aspect the invention provides a wearable device for dispensing an air treatment chemical, where the device has:

(a) a housing including an inlet for permitting air to enter into an interior space of the housing and including an outlet for permitting air mixed with air treatment chemical to exit the interior space;

(b) a substrate positioned in the housing, the substrate bearing an air treatment chemical;

(c) a power supply mounted to the housing;

(d) a motor mounted in the housing, the motor being powered by the power supply; and (e) a fan mounted in the housing, the fan being capable of moving air from the inlet adjacent the substrate so as to mix air treatment chemical into the moving air, and then deliver a mixture of air and air treatment chemical through the outlet to outside of the housing, the fan including a rotor connected to the motor and a plurality of spaced apart blades connected to and extending away from the rotor.

In one form, the device can maintain an average volumetric flow rate of air of at least 1.5 cubic feet per minute (cfm) (0.042 m$^3$/min.) over a twelve hour period with the device consuming from the power supply 0.35 watts or less of power for the twelve hour period.

In particularly preferred forms of this aspect of the invention the fan includes 12 to 18 blades (e.g. 13 to 15 blades, e.g. 14 blades), and each blade has a body extending from an inner edge to an outer edge, the inner edge of each blade being spaced a distance from a centerpoint of the rotor along a radial line from the centerpoint of the rotor, the body of a plurality of such blades:

(a) forming an included angle with its associated radial line in the range of 100 to 150 degrees; and/or (b) having a length measuring 80% to 130% of a distance from a centerpoint of the rotor to the inner edge of the blade; and/or (c) having a length measuring 45% to 75% of a distance from a centerpoint of the rotor to the outer edge of the blade; and/or (d) having a length from a centerpoint of the rotor to an outer edge of the rotor of 10 to 50 millimeters.

The rotor can include a central wall spaced inward from a perimeter of the rotor and the wall defines a recess in the rotor. At least a portion of the motor is positioned in the recess, and the blades extend from the wall radially outward toward the perimeter of the rotor.

In other preferred forms the housing has a plurality of spaced apart openings, the openings being spaced around at least 180 degrees (more preferably at least 235 degrees) of a side structure of the housing, and a plurality of the blades are substantially perpendicular to a front wall of the housing, the front wall of the housing having an array of inlet apertures. The device can produce an average volumetric flow rate of air of at least 1.5 cubic feet per minute over a twelve hour period (preferably for an even longer period), yet is so efficient in energy use and power requirements more compact batteries (e.g. AAA rather than AA) can be used to power the device. This not only makes the device more compact from that factor, this permits the batteries to be positioned in an otherwise unavailable location, thereby further reducing the size and weight of the device.

In another aspect the invention provides a wearable device for dispensing an air treatment chemical, where the device has:

(a) a housing including an inlet for permitting air to enter into an interior space of the housing and including an outlet for permitting air mixed with air treatment chemical to exit the interior space;

(b) a substrate positioned in the housing, the substrate bearing an air treatment chemical;

(c) a power supply mounted to the housing;

(d) a motor mounted in the housing, the motor being powered by the power supply;

(e) a fan connected to the motor, the fan being capable of moving air from the inlet adjacent the substrate so as to mix air treatment chemical into the moving air, and then deliver a mixture of air and air treatment chemical through the outlet to outside of the housing; and (f) a clip rotatably connected to an outer wall of the housing.

Preferred forms of this device are where one of the clip and the outer wall of the housing includes a projection, the other of the clip and the outer wall of the housing includes an arcuate well, and the projection moves in the well when rotating the clip. For example, the well can be dimensioned such that the clip can rotate at least 90 degrees, and there can be a means for indexed rotational positioning of the housing and the clip relative to each other. This latter feature can be a detent system where there is a flexible tab on one of the clip and housing, and a series of distinct rest positions for the tab on another of the clip and housing. For example, each such rest position can be in the form of a depression, and the tab can have a projection thereon.

In yet another aspect of the invention there is provided a wearable device for dispensing an air treatment chemical, the device having:

(a) a housing including a first main housing section and a second lid housing section, the first main housing section and the second lid housing section defining an interior space of the housing when the first main housing section and the second lid housing section are in a closed position, the housing having an inlet for permitting air to enter into an interior space of the housing, and an outlet for permitting air mixed with air treatment chemical to exit the interior space;

(b) a substrate positioned in the interior space of the housing, the substrate bearing an air treatment chemical;

(c) a power supply mounted to the housing;

(d) a motor mounted in the interior space of the housing, the motor being powered by the power supply;

(e) a fan connected to the motor, the fan being capable of moving air from the inlet adjacent the substrate so as to mix air treatment chemical into the moving air, and then deliver a mixture of air and air treatment chemical through the outlet to outside of the housing; and (f) a hinge mechanism connecting the first main housing section and the second lid housing section for governing pivotal movement between a closed position and an open position of the second lid housing section relative to the first main housing section, the hinge mechanism comprising a pair of spaced apart hinge arms mounted on the second lid housing section, and a pair of spaced apart notches positioned on the first main housing section, each hinge arm including a pivot pin, each pivot pin capable of rotating within an associated one of the notches.

In preferred forms of this aspect of the invention the pivot pin of each hinge arm extends laterally adjacent an end of the hinge arm, each such pivot pin having an outer wall having a flat section, and the flat section of each such pivot pin is mounted in a notch to contact a flat surface of its associated notch when the second lid housing section is in the fully open position.

Each such pivot pin may also have on an outer wall a second flat section, and the second flat section of each pivot pin contacts a flat surface of its associated notch when the second lid housing section is in the fully open position. For example, the notches can be generally rectangular. These structures are most useful when their is a frame in the housing for supporting the substrate, the frame including a pair of slots, and each of the hinge arms moves within one of the slots during pivotal movement between the closed position and the fully open position of the second lid housing section.

Hence, it should be appreciated that the devices of the present invention have more efficient power usage, thereby permitting smaller power supplies and in any event a more compact and more lightweight assembly. Further, these devices make it more comfortable for the device to be operated even when the consumer is sitting and also provide greater control of the dispensing direction. Also, the special hinging and notch arrangement holds the lid open during replacement of the refill of active, but will cause the lid to snap to the closed once the lid is moved to a defined midpoint. This facilitates refill replacement.

These improvements lower the cost of production, permit the device to be operated at lower cost, and meets consumer preferences to minimize the weight of the device if a device like this is to be used.

These and other advantages of the present invention will become better understood upon consideration of the following detailed description and drawings.

DETAILED DESCRIPTION OF THE INVENTION

A preferred example wearable chemical dispenser 18 is shown in FIGS. 1-11. The wearable chemical dispenser 18 includes a top housing section 20 having a generally oblong side wall 22 that extends from a top wall 23. In use, the wall 23 is typically frontally disposed and acts as a lid. A plurality of spaced apart apertures 24 are radially arranged in the top wall 23 of the top housing section 20. The apertures 24 provide an inlet for permitting air to enter into an interior space of the wearable chemical dispenser 18. A tab 26 provides a means to grasp the top housing section 20 when opening the top housing section 20.

The wearable chemical dispenser 18 also includes a slide cover 28 having an on-off button 29, openings 31, and a cam projection 32. A fastener 34 (see FIG. 6) mounts the slide cover 28 to the top housing section 20 such that the slide cover 28 may rotate with respect to the top housing section 20 when a user moves the on-off button 29 along the side wall 22 of the top housing section 20. In the 'off' position, the slide cover 28 closes the apertures 24 that are radially arranged in the top wall 23 of the top housing section 20. In the 'on' position, the openings 31 of the slide cover 28 align with the apertures 24 that are radially arranged in the top wall 23 of the top housing section 20.

Figure 1:
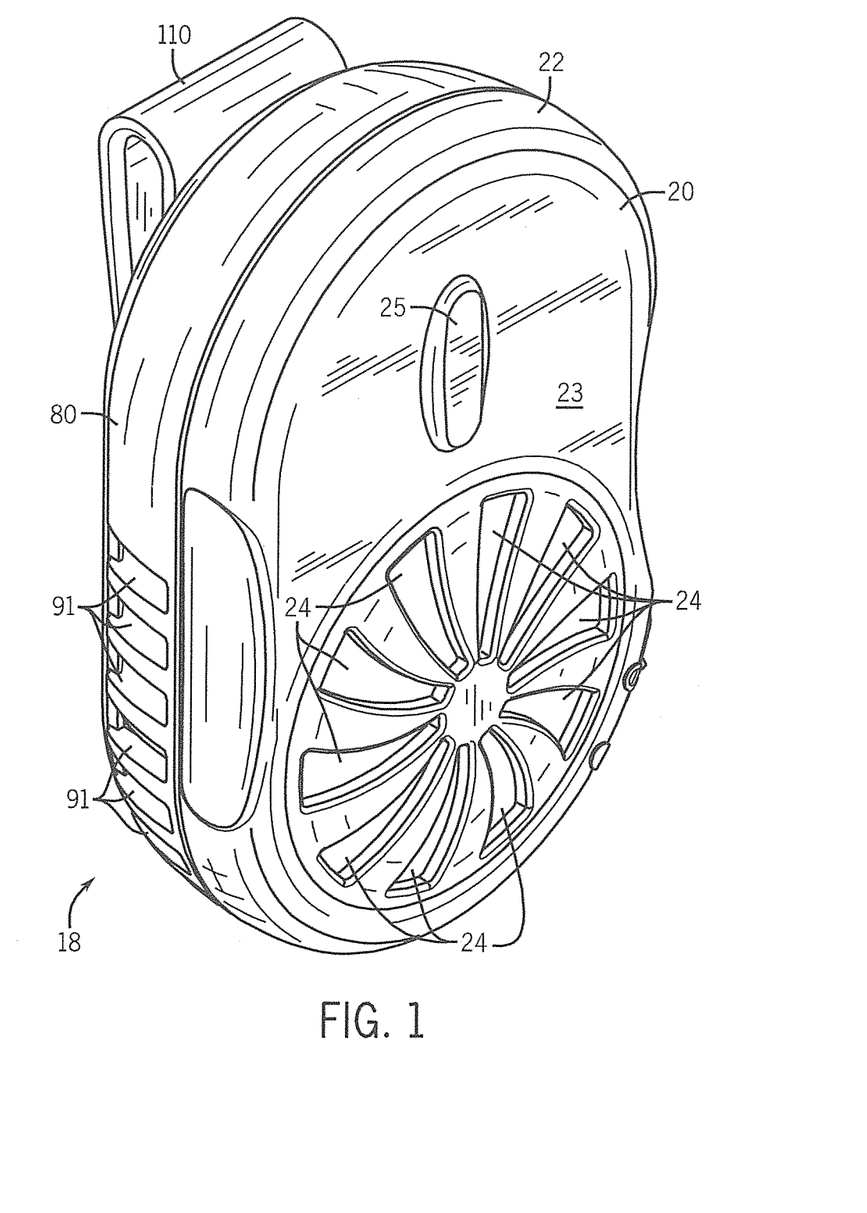
FIG. 1 is a left, top, frontal perspective view of a wearable chemical dispenser according to the invention.
Figure 2:
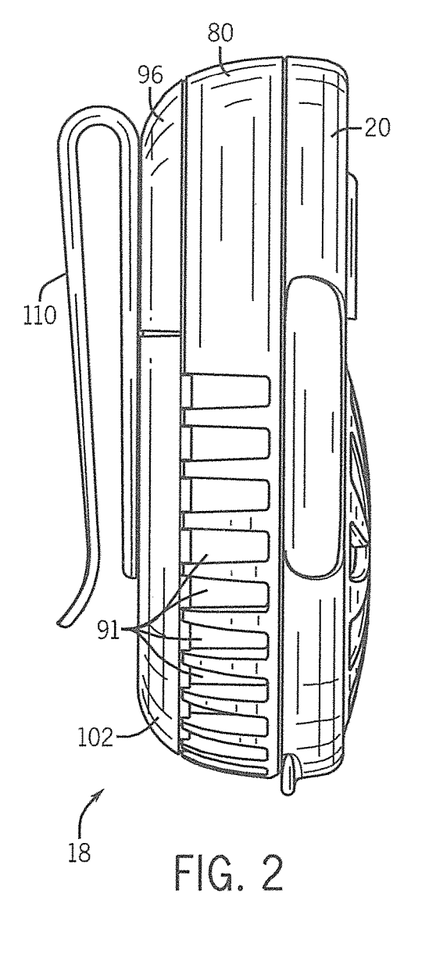
FIG. 2 is a left side elevational view of the dispenser of FIG. 1.
Figure 3:
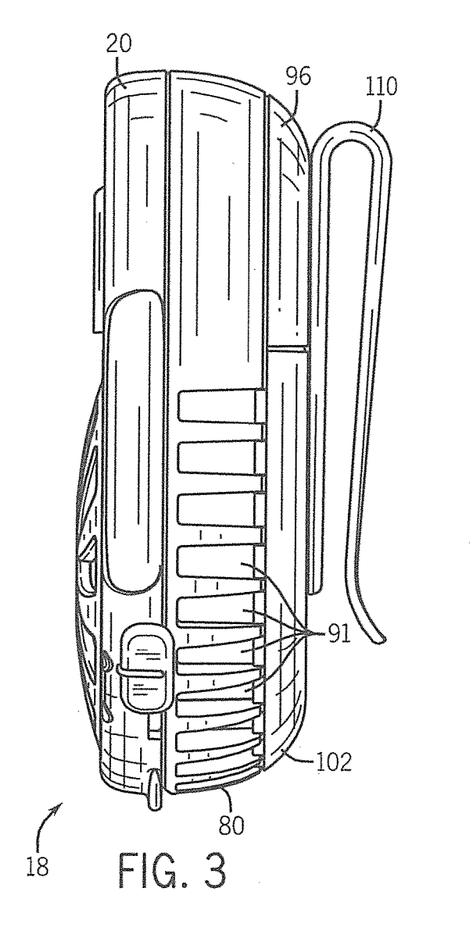
FIG. 3 is a right side elevational view of the dispenser of FIG. 1.
Figure 4:
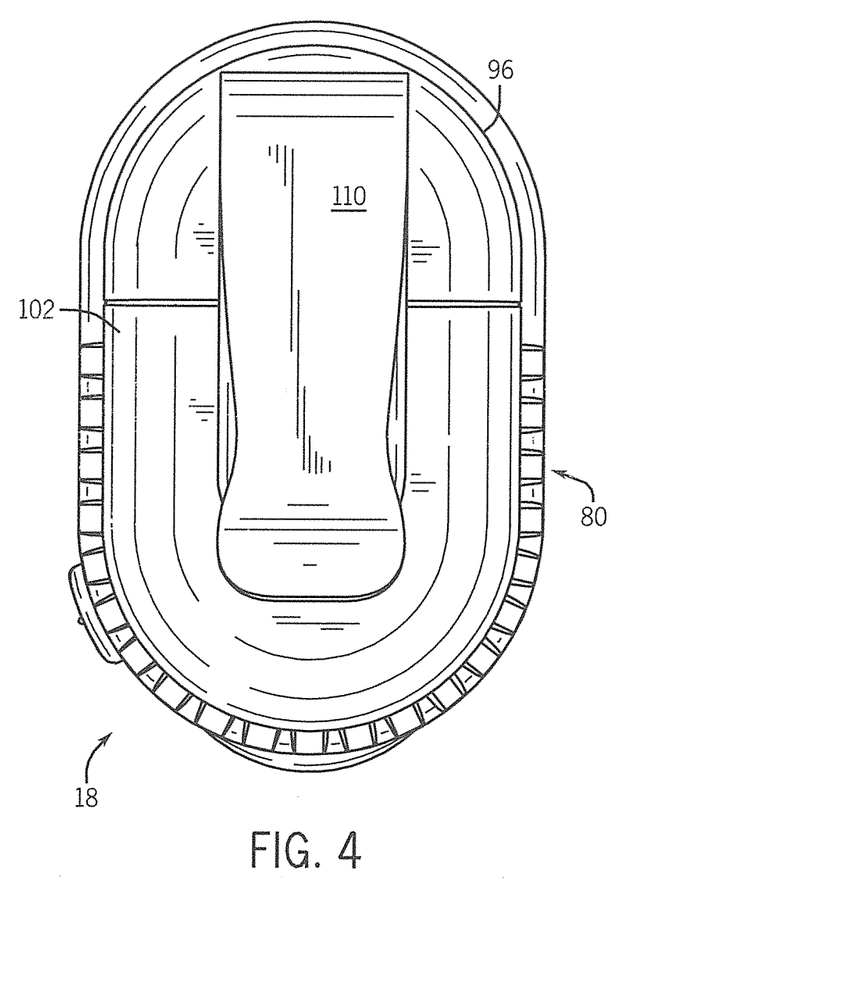
FIG. 4 is a rear elevational view of the dispenser of FIG. 1.
Figure 5:
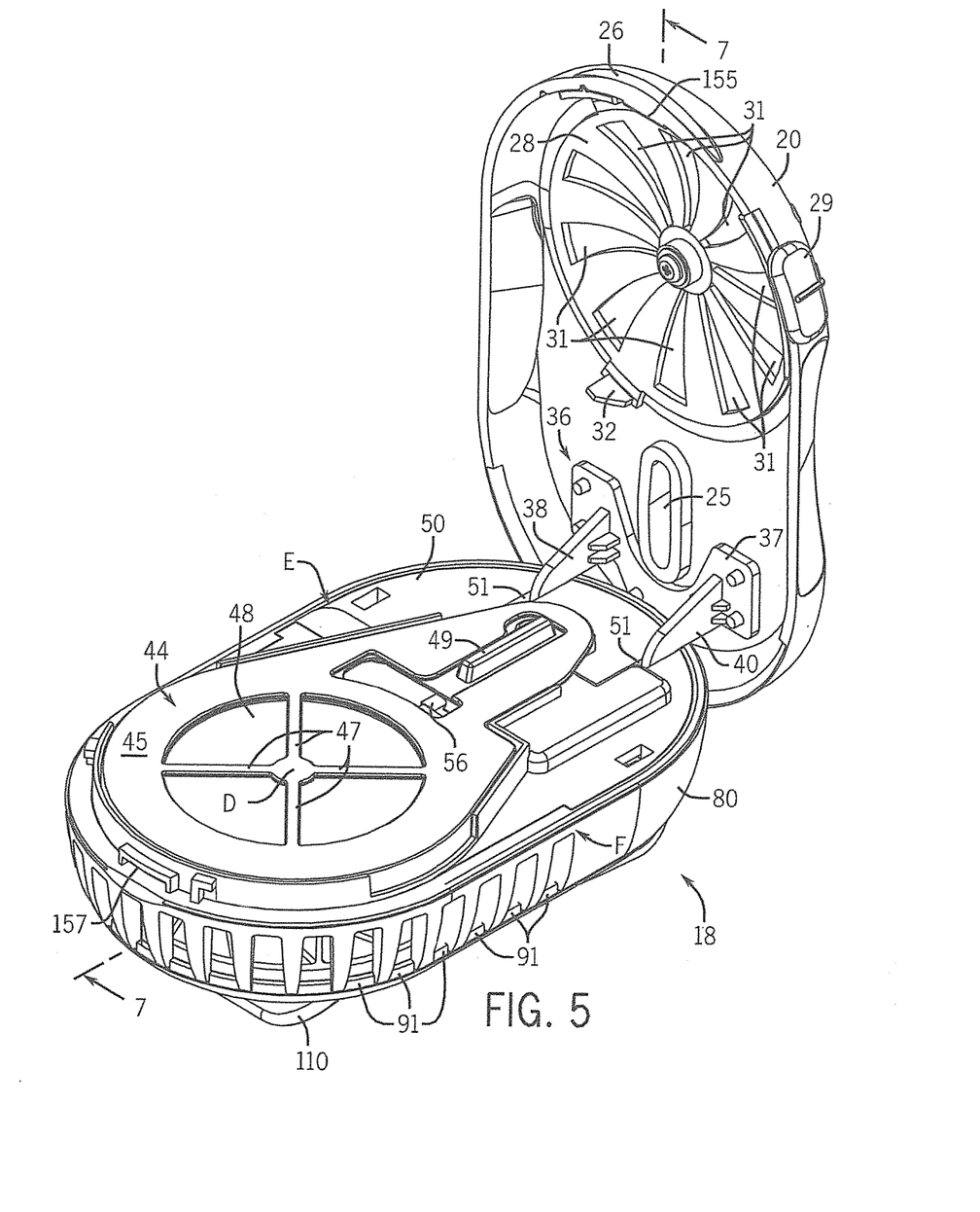
FIG. 5 is a right, bottom perspective view of the dispenser of FIG. 1, albeit with the lid in an open position.
Figure 6:
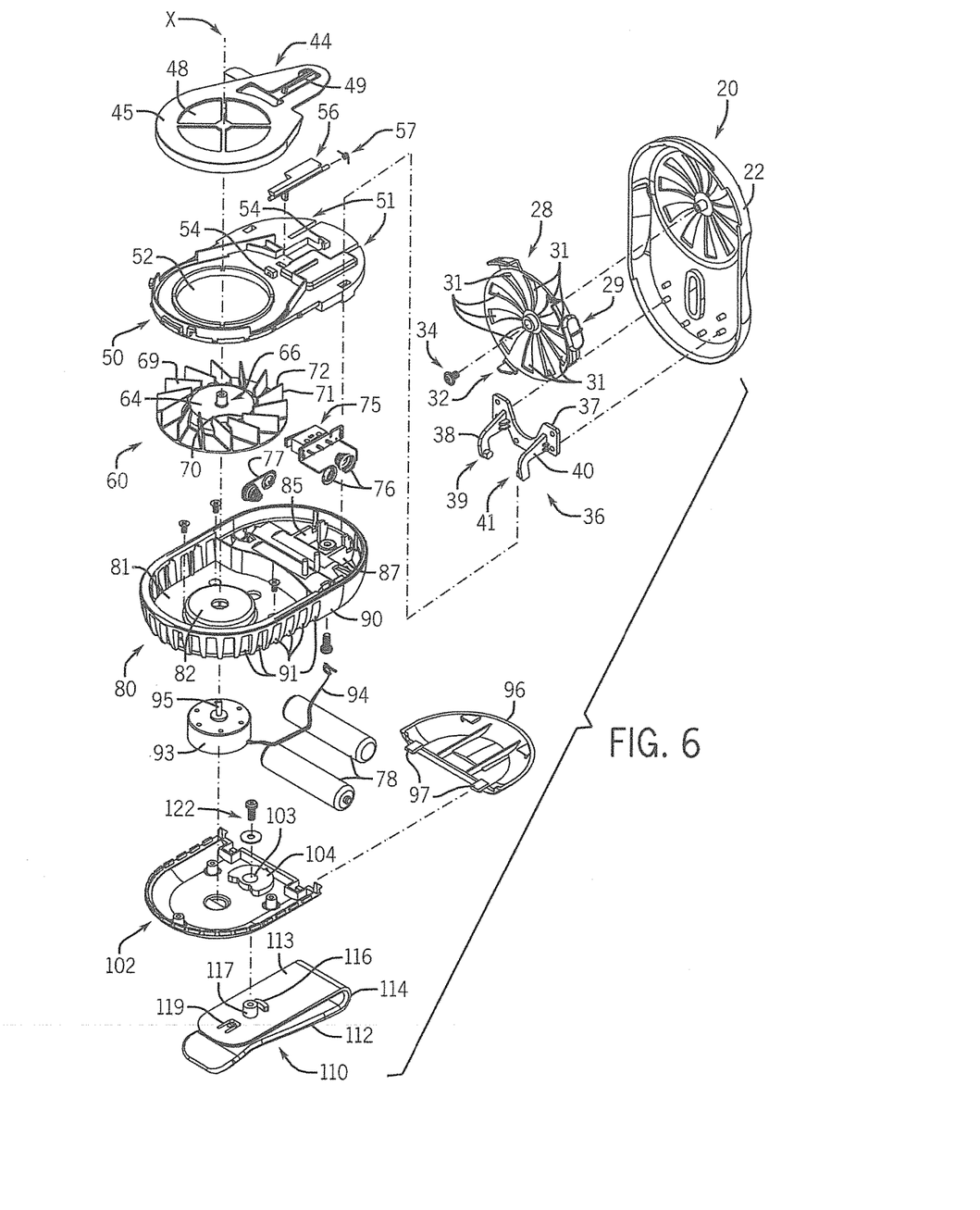
FIG. 6 is an exploded perspective view of the dispenser of FIG. 1.

The wearable chemical dispenser 18 also includes a hinge bracket 36 that is mounted to an inner surface of the top housing section 20 as shown in FIG. 5. The hinge bracket 36 has a flat base plate 37 that mounts to the top housing section 20, a generally L-shaped arm 38 having an inwardly directed pivot pin 39 at its end, and generally L-shaped arm 40 having an inwardly directed pivot pin 41 at its end. The arm 38 and the arm 40 are spaced apart on the plate 37 as shown in FIGS. 5 and 6. The hinge bracket 36 forms part of a hinge mechanism as described below.

A replaceable refill unit 44 is provided with the wearable chemical dispenser 18. The refill unit 44 has a generally slab-like support structure 45. In top plan view, the refill unit 44 has an essentially tear-drop shaped overall appearance, with a generally circular portion at one end and a generally triangular portion at another end. There is a spoke support 47 across a circular opening through the refill unit 44 (see FIG. 5). Across the spoke support 47 is positioned a fabric substrate 48. When air is drawn in, the air passes through the fabric substrate 48. The choice of the fabric, and its porosity, the speed of the air flow, and the vapor pressure of the active, are the main factors in coordinating the speed of use up of the active with the speed of use up of a visual use-up cue 49 (see FIG. 5) that can be viewed through the slot 25 of the top housing section 20. An example refill unit has a twelve hour life, and the visual use-up cue 49 is designed to evaporate or change in appearance after twelve hours. A suitable visual use-up cue is described in U.S. Patent Application Publication No. 2008/0141928.

By impregnating the fabric substrate 48 with an appropriate air treatment chemical, air entering the device will pick up some of the volatile chemical, and dispense it out of the device. Active release rates of 0.2 milligrams per hour (mg./hr.) or higher are preferred. Particularly preferred actives are transfluthrin, prallethrin, vaporthrin, tefluthrin, and esbiothrin or other synthetic pyrethroids. For use in controlling mosquitoes, it is preferred to use metofluthrin from the Sumitomo Chemical Company (trade name Sumi-One). The impregnation material can be pure active, or for ease of handling the material can be dissolved in a hydrocarbon or other solvent. Alternatively, or in addition, the fabric may also bear a fragrance, a deodorizer, or other air treatment chemical. It is preferred to have the fabric substrate 48 configured so that the pressure drop across the substrate is no more than 40 Pascals (Pa). Suitable fabrics can be made of woven or non-woven materials providing only minimal resistance to the airflow.

The fabric substrate 48 should also be capable of holding active ingredient dosed onto the material and also allow ready migration of the active to the surface so as to allow its evaporation in response to the airflow. For an active ingredient that is hydrophobic and migrateable at common environmental temperatures between about 10° C. and 40° C. (e.g., metofluthrin), suitable materials include, only by way of example, polyester, polypropylene, cotton, cellulose, poly-rayon, and other similar fabrics. These can be non-wovens with basis weights ranging from 10 grams per square meter (gsm) to 40 grams per square meter (gsm), fabricated from synthetic, natural, or combined synthetic and natural polymeric materials.

The ideal fabric substrate 48 should also allow for wicking of the active ingredient following dosing so as to ensure efficient distribution throughout the substrate, and thereafter allow migration of active ingredient to the substrate surface to replenish the active ingredient that is being evaporated by the passing airflow. Dosing may be by dropping, spraying, printing, or other conventional delivery of a liquid active ingredient to the substrate. A particularly desirable fabric is a non-woven felted material with a basis weight of 20-30 gsm fabricated from polyethylene terephthalate.

A frame 50 is located below the refill unit 44 in the wearable chemical dispenser 18. The frame 50 has a generally oblong perimeter, and supports the refill unit 44 (see FIGS. 5 and 6). Note that one side of the essentially triangular portion of the refill unit 44 is straight and the other is indented. This slight lack of symmetry is designed to accommodate a corresponding slight lack of symmetry along the top side of frame 50, and to thereby prevent a consumer from installing the refill unit 44 inside-out on the frame 50. One end of the frame 50 has a pair of slots 51 that form part of a hinge mechanism as described below. A circular opening 52 is provided at the other end of the frame 50. Holes 54 in the frame 50 support a rotating activation button 56 that is biased by a rotary spring 57 into an off position.

Figure 11:
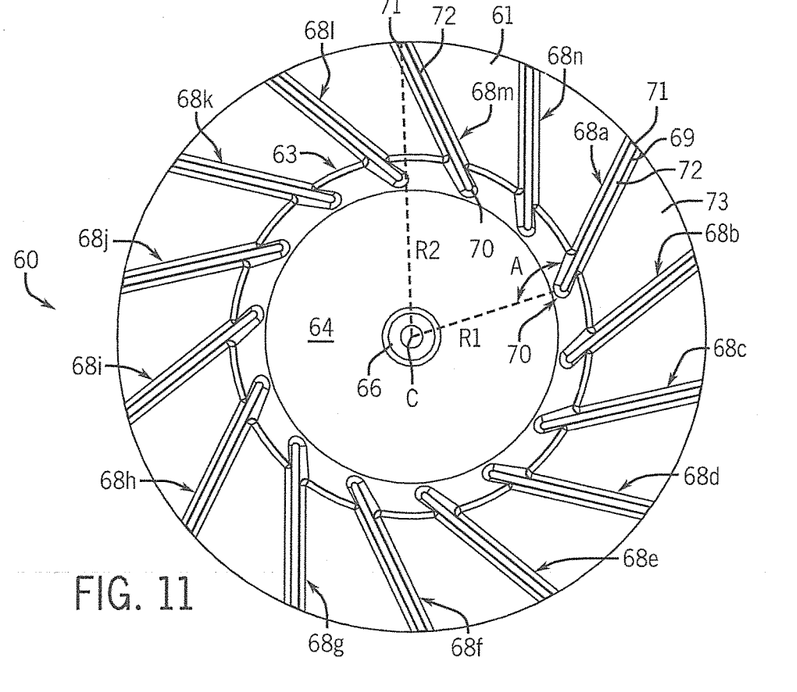
FIG. 11 is a top view of the rotor fan of the dispenser of FIG. 1.

Looking at FIGS. 6 and 11, there is shown a fan 60 of the wearable chemical dispenser 18. The fan 60 has a rotor 61 having a central vertical wall 63 that joins a top central horizontal wall 64. The central vertical wall 63 and the top horizontal wall 64 define a recess 65 in the bottom of the rotor 61 (see FIG. 7). The top horizontal wall 64 of the rotor 61 includes a tubular mounting element 66 on the axis of the rotor 61.

The preferred fan 60 includes fourteen fan blades 68a to 68n (see FIG. 11). It has been discovered that a fan configuration, which results in an ideal balance of airflow and minimal power consumption for the wearable chemical dispenser 18, includes twelve to eighteen fan blades. Preferably, the fan produces an average volumetric flow rate of air of 1.5 to 3 cubic feet per minute (with the refill unit 44 installed) over the life (e.g., at least eight, and most preferably at least twelve hours) of a refill unit 44. Typically, the fan will operate at 3000-5000 rpm. In one example wearable chemical dispenser 18, over the life (e.g., twelve hours) of a refill unit 44, the consumed power from the power supply is 0.35 watts or less, preferably 0.30 watts or less, more preferably 0.25 watts or less, and even more preferably 0.20 watts or less. In one example embodiment, over a twelve hour life of a refill unit 44, the consumed power from the power supply is about 0.17 watts while maintaining an average volumetric flow rate of air of at least 1.5 cubic feet per minute over the twelve hour period. When using one or more batteries for the power supply, the voltage will vary during discharge. However, the power consumed can be determined from the total energy consumed divided by the total time.

Each blade 68a to 68n has a generally rectangular body 69 defined by an inner edge 70, an outer edge 71, a top edge 72 extending from the inner edge 70 to the outer edge 71, and top surface 73 of the rotor 61. Looking at FIG. 11, a radial reference line $R_1$ can be extended from a centerpoint C of the rotor 61 to the inner edge 70 of each blade 68a to 68n. Likewise, a radial reference line $R_2$ can be extended from a centerpoint C of the rotor 61 to the outer edge 71 of each blade 68a to 68n. The body 69 of each blade 68a to 68n forms an included angle A with its associated radial reference line $R_1$.

It has been discovered that a fan configuration, which results in an ideal balance of airflow and minimal power consumption for the wearable chemical dispenser 18, includes a range of fan sizes and fan blade angles. Preferably, each blade 68a to 68n has a length extending from the inner edge 70 to the outer edge 71 in which the length measures 80% to 130% of the distance of radial reference line $R_1$. Preferably, each blade 68a to 68n has a length extending from the inner edge 70 to the outer edge 71 in which the length measures 45% to 75% of the distance of radial reference line $R_2$. Preferably, the included angle A in FIG. 11, which is formed between the body 69 of each blade 68a to 68n and its associated radial reference line $R_1$, is in the range of 100 to 150 degrees. These example fan sizes and fan blade angles contribute to an ideal balance of airflow and minimal power consumption for the wearable chemical dispenser 18. Thus, among other things, the average volumetric flow rate of air from the fan depends on the outer radius of the rotor, the inner radius of the rotor, the number of blades, the blade angles, and the fan revolutions per minutes.

One non-limiting example of the fan 60 has a length extending from the inner edge 70 to the outer edge 71 of about 15 millimeters, a radial reference line $R_1$ of about 14 millimeters, a radial reference line $R_2$ of about 25 millimeters, and an included angle A of about 120 degrees. In this non-limiting example, blade thicknesses can range from 0.3-1.0 millimeters, with 0.6 millimeters being preferred, and blade height (from the top surface 73 of the rotor 61 to the top edge 72 of the body 69) can range from 5-11 millimeters, with about 8 millimeters being preferred.

The wearable chemical dispenser 18 includes an electrical power supply. In the example embodiment shown, a microswitch 75 of the power supply is electrically connected to battery contacts 76. Another battery contact 77 completes an electrical circuit with batteries 78 and the battery contacts 76 to provide electricity to the microswitch 75. When a user rotates the slide cover 28 by rotating the on-off button 29 into the 'on' position, the cam projection 32 of the slide cover 28 is driven into the rotating activation button 56 which then contacts the microswitch 75 to turn on the power supply.

Figure 7:
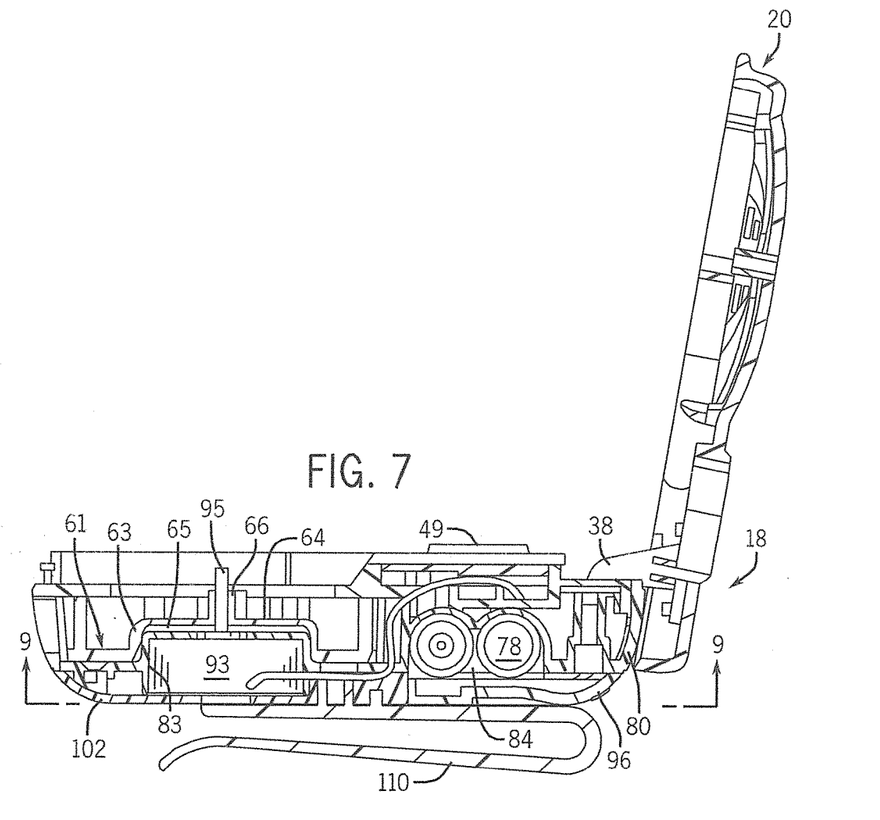
FIG. 7 is a cross-sectional view taken along line 7-7 of FIG. 5.
Figure 8:
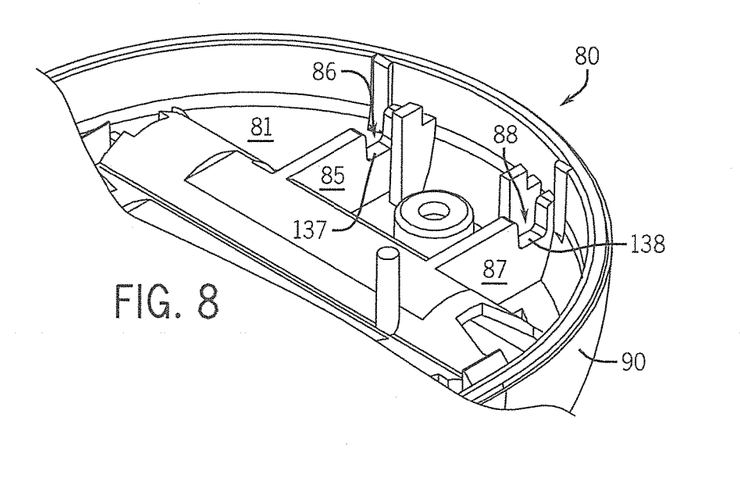
FIG. 8 is an enlarged detailed perspective view focusing on the hinge supports of the dispenser of FIG. 1.

Looking at FIGS. 6-8, the wearable chemical dispenser 18 includes a chassis 80 for mounting various components of the wearable chemical dispenser 18. When the top housing section 20 and the chassis 80 are in a closed position (see, e.g., FIG. 1), a housing having an interior space is formed. The chassis 80 engages the frame 50 in a snap fit.

The chassis 80 has a bottom wall 81 with a raised portion 82 that defines a upwardly directed space 83 in the chassis 80 (see FIGS. 6 and 7). A battery compartment 84 is also provided in the bottom wall 81 of the chassis 80 (see FIG. 7). The battery contacts 76, 77 are mounted at opposite ends of the battery compartment 84. Extending upward from the bottom wall 81 of the chassis 80 there is a hinge support 85 having a notch 86 and a hinge support 87 having a notch 88 (see FIGS. 6 and 8). The hinge support 85 and the hinge support 87 form part of a hinge mechanism as described below.

The chassis 80 also includes a side wall 90 having regularly spaced openings 91 that define an outlet for permitting air mixed with air treatment chemical to exit the interior space of the wearable chemical dispenser 18. In the non-limiting example embodiment shown in FIG. 5, the openings 91 extend from point E to point F around the side wall 90 of the chassis 80. In FIG. 5, the included angle between point E and point F and point D (which is on axis X shown in FIG. 6) is about 270 degrees. Therefore, the openings 91 are regularly spaced around 270 degrees of the side wall 90 of the chassis 80. Preferably, the openings 91 are regularly spaced around at least 180 degrees of the side wall 90 of the chassis 80. More preferably, the openings 91 are spaced around at least 235 degrees of the side wall 90 of the chassis 80. One non-limiting example of the total outlet area of the openings 91 is $8.5 \times 10^{-4}$ m$^2$. Advantageously, the battery compartment 84 is isolated from the openings 91. These example opening configurations contribute to an ideal balance of airflow and minimal power consumption for the wearable chemical dispenser 18.

Preferably, a flow path from the fan to the openings 91 is unobstructed. Some other devices included a slide cover designed to shut off air flow by blocking the inlet vents and the exhaust vents. The intent was to minimize loss of actives while the unit is not in use by blocking off airflow across the dosed pad. The walls blocking the exhaust vents and the geometries supporting them occupied large space and caused the device to increase in size. These blocking walls are eliminated in the present invention without increased loss in actives ingredient.

A motor 93 is positioned in the space 83 in the chassis 80, and a wire 94 connects the motor 93 to the microswitch 75 for powering the motor when the rotating activation button 56 contacts the microswitch 75 to turn on the power supply. The motor 93 includes a drive shaft 95 that is connected to the tubular mounting element 66 on the rotor 61. As a result, the motor 93 can rotate the fan 60. A battery door 96 covers the battery compartment 84 in the bottom wall 81 of the chassis 80. The battery door 96 includes mounting tabs 97. A bottom cover 102 is fastened to the chassis 80 by way of fasteners.

Figure 9:
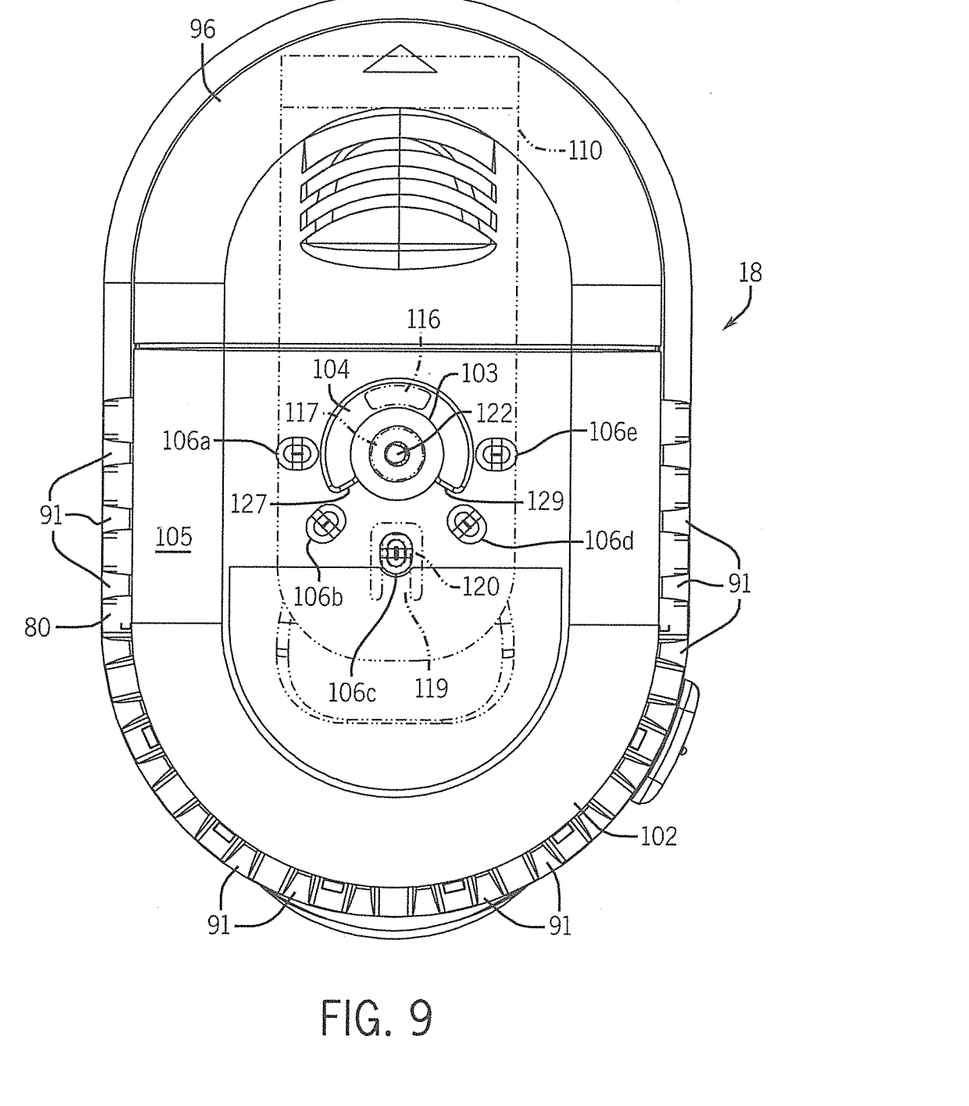
FIG. 9 is a view taken along line 9-9 of FIG. 7, albeit with the clip added in phantom to show where its relative position would be if viewable in rear view.
Figure 10:
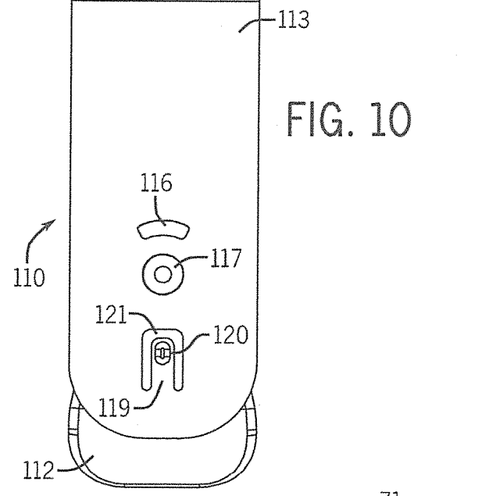
FIG. 10 is an enlarged frontal view of the rotating clip of the dispenser of FIG. 1 by itself.

Looking now at FIGS. 6, 9 and 10, means for clipping the wearable chemical dispenser 18 to a user's clothing (e.g., a belt) are shown. The bottom cover 102 includes a throughhole 103 partially surrounded by an arcuate well 104 in a bottom surface 105 of the bottom cover 102. The bottom surface 105 of the bottom cover 102 further includes five spaced apart oblong depressions 106a, 106b, 106c, 106d, 106e arranged in a semicircle around the throughhole 103. The wearable chemical dispenser 18 also includes a clip 110 having a front section 112 that is spaced at its upper end from a rear section 113 by a top section 114 that connects the front section 112 and the rear section 113. At the lower end of the clip 110, the front section 112 and the rear section 113 are in contact until flexed apart by a user. The rear section 113 of the clip 110 has an arcuate projection 116, a tubular mounting element 117, and a moveable tab 119 having a protrusion 120 on its end. The moveable tab 119 is formed by a cutout 121 in the rear section 113 of the clip 110. A fastener 122 (see FIG. 6) is inserted through the throughhole 103 of the bottom cover 102 and into the tubular mounting element 117 of the clip 110 to connect the bottom cover 102 and the clip 110.

Still looking at FIGS. 6, 9 and 10, a rotation feature of the clip 110 can be explained. When the clip 110 is connected to the bottom cover 102, the clip 110 is positioned as in FIG. 9. The fastener 122 secures the tubular mounting element 117 of the clip 110 in the throughhole 103 of the bottom cover 102 such that the clip 110 can rotate with respect to the bottom cover 102. When the clip 110 is rotated clockwise from its position shown in FIG. 9, the arcuate projection 116 moves in the arcuate well 104 in a clockwise direction thereby guiding rotation of the clip 110. The protrusion 120 of the moveable tab 119 moves out of the depression 106c by way of flexing of the moveable tab 119. The clip 110 rotates clockwise until the protrusion 120 of the moveable tab 119 moves into the depression 106b of the bottom cover 102. When the clip 110 is further rotated clockwise from the position in which the protrusion 120 is in the depression 106b, the arcuate projection 116 moves further clockwise in the arcuate well 104, and the protrusion 120 moves out of the depression 106b by way of flexing of the moveable tab 119. The clip 110 rotates clockwise until the protrusion 120 of the moveable tab 119 moves into the depression 106a of the bottom cover 102. When in this position, the arcuate projection 116 is prevented from moving further clockwise by wall 129 of the arcuate well 104, and the housing of the wearable chemical dispenser 18 is at 90 degrees in relation to the clip 110.

When the clip 110 is rotated counterclockwise from its position shown in FIG. 9, the arcuate projection 116 moves in the arcuate well 104 in a counterclockwise direction thereby guiding rotation of the clip 110. The protrusion 120 of the moveable tab 119 moves out of the depression 106c by way of flexing of the moveable tab 119. The clip 110 rotates counterclockwise until the protrusion 120 of the moveable tab 119 moves into the depression 106d of the bottom cover 102. When the clip 110 is further rotated counterclockwise from the position in which the protrusion 120 is in the depression 106d, the arcuate projection 116 moves further counterclockwise in the arcuate well 104, and the protrusion 120 moves out of the depression 106d by way of flexing of the moveable tab 119. The clip 110 rotates counterclockwise until the protrusion 120 of the moveable tab 119 moves into the depression 106e of the bottom cover 102. When in this position, the arcuate projection 116 is prevented from moving further counterclockwise by wall 127 of the arcuate well 104, and the housing of the wearable chemical dispenser 18 is at 90 degrees in relation to the clip 110.

Thus, the arcuate projection 116 and the arcuate well 104 provide a means for controlled rotation of the clip 110 with respect to the bottom cover 102. Specifically; the projection 116 moves in the well 104 when rotating the clip 100. In the example embodiment of FIG. 9, the well 104 and the projection 116 are dimensioned such that the clip 110 can rotate 180 degrees (i.e., 90 degrees clockwise and 90 degrees counterclockwise). Preferably, the clip 110 can rotate at least 90 degrees.

In addition, the moveable tab 119 with the protrusion 120 and the spaced apart oblong depressions 106a, 106b, 106c, 106d, 106e arranged in a semicircle around the throughhole 103 provide a means for indexed rotational positioning of the clip 100 and the housing relative to each other. The depressions 106a, 106b, 106c, 106d, 106e provide a guide and the protrusion 120 of the moveable tab 119 travels stepwise in the guide as explained above.

Often a user will clip the wearable chemical dispenser 18 to a belt with the clip 110 of the wearable chemical dispenser 18 in the position shown in FIG. 9 wherein the outlet openings 91 face down from, to one side, and to the opposite side of the user. This directs a mixture of air and air treatment chemical down from, to one side, and to the opposite side of the user. If a user wishes to direct the mixture of air and air treatment chemical up, down, and to one side, the user can rotate the housing using the rotating clip 110 as described above. A user may also wish to rotate the housing in order to avoid any pinching against the body when sitting. Also, by locating a pivot point of the clip 110 in a section of the housing adjacent the outlet openings 91, more precise control of the direction of the mixture of air and air treatment chemical is afforded when rotating the clip 110. Thus, the housing of the wearable chemical dispenser 18 can be vertical or horizontal when in use.

Turning now to FIGS. 5, 6, 8, 8A, 8B, and 8C, the hinge mechanism of the wearable chemical dispenser 18 can be described further. The hinge mechanism allows a user to open the top housing section 20 to the open position of FIGS. 5, 7 and 8A so that a new refill unit 44 can be installed on the frame 50 as shown in FIG. 5.

Figure 8A:
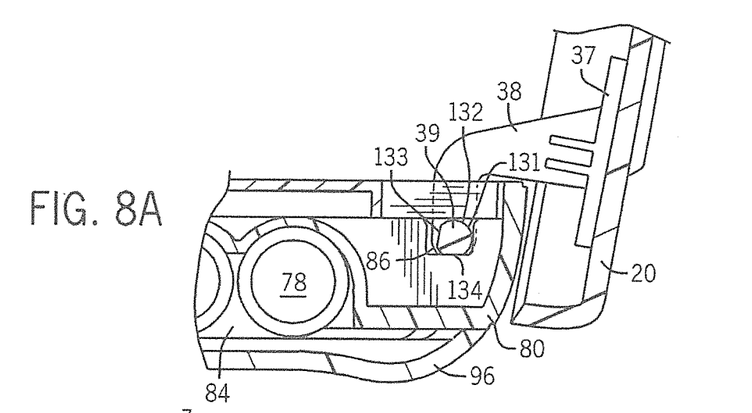
FIG. 8A is an enlarged detailed cross-sectional view of one arm of the hinge in one hinge support, with the lid in a fully open position.
Figure 8B:
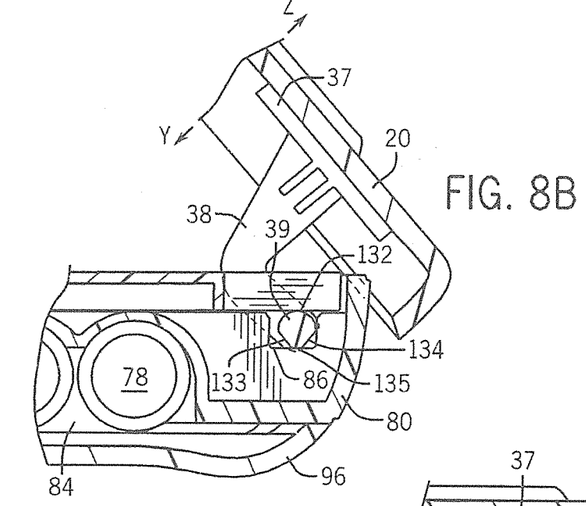
FIG. 8B is a view similar to FIG. 8A, but with the lid instead in only a partially open position.
Figure 8C:
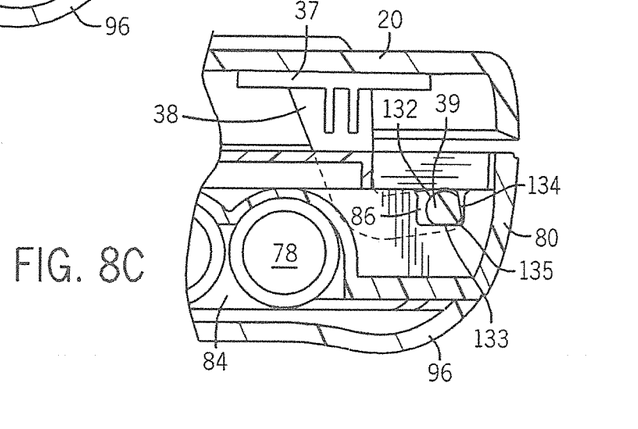
FIG. 8C is a view similar to FIG. 8A, but with the lid instead in the closed position.

Looking at FIGS. 8A, 8B and 8C, movement of the pivot pin 39 of the hinge arm 38 in the notch 86 of the hinge support 85 can be explained. The pivot pin 39 has an outer wall 131 having an arcuate section 132 that extends between a first flat section 133 and a second flat section 134. An intermediate section 135 connects the first flat section 133 and the second flat section 134. Although FIGS. 8A, 8B and 80 do not show the pivot pin 41, the pivot pin 41 has an outer wall with the same shape as outer wall 131 of pivot pin 39.

In FIG. 8A, the top housing section 20 is in a fully open position. The second flat section 134 of the outer wall 131 of the pivot pin 39 rests on a bottom flat surface 137 (see FIG. 8) of the notch 86 of the hinge support 85. The mating of the bottom flat surface 137 of the notch 86 and the second flat section 134 of the outer wall 131 of the pivot pin 39 keeps the top housing section 20 in the fully open position.

In FIG. 8C, the top housing section 20 is in a closed position. The first flat section 133 of the outer wall 131 of the pivot pin 39 rests on the bottom flat surface 137 of the notch 86 of the hinge support 85. The mating of the bottom flat surface 137 of the notch 86 and the first flat section 133 of the outer wall 131 of the pivot pin 39 keeps the top housing section 20 in the closed position. Also, a catch 155 (see FIG. 5) of the top housing section 20 engages a slot 157 (see FIG. 5) to keep the housing closed.

In FIG. 8B, the top housing section 20 is in a partially open position. The intermediate section 135 of the outer wall 131 of the pivot pin 39 rests on the bottom flat surface 137 of the notch 86 of the hinge support 85. The mating of the bottom flat surface 137 of the notch 86 and the intermediate section 135 of the outer wall 131 of the pivot pin 39 tends to keep the top housing section 20 in the partially open position. However, movement of the top housing section 20 in direction Z will cause the top housing section 20 to quickly return to the fully open position shown in FIG. 8A as pivot pin 39 will rotate due to gravity until the second flat section 134 of the outer wall 131 of the pivot pin 39 rests on a bottom flat surface 137 of the notch 86. In contrast, movement of the top housing section 20 in direction Y will cause the top housing section 20 to move to the closed position shown in FIG. 8C as pivot pin 39 will rotate due to gravity until the first flat section 133 of the outer wall 131 of the pivot pin 39 rests on a bottom flat surface 137 of the notch 86.

The pivot pin 41 moves in the notch 88 in a similar manner with flat sections of the outer wall of the pivot pin 40 resting on the bottom flat surface 138 (see FIG. 8) of the notch 88 of the hinge support 87 during opening of the top housing section 20. During movement of the hinge, the arm 38 and the arm 40 of the hinge bracket 36 move in the slots 51 of the frame 50 (see FIG. 5).

The configuration of the outer wall of the pivot pins 39, 41 of the arms 38, 40 of the hinge bracket 36 provides an advantageous hinging action when opening the top housing section 20. When a user first begins to open the top housing section 20, the user must overcome the tendency of the pivot pins 39, 41 to return to the closed position where the first flat section of the outer wall of the pivot pin rests on a bottom flat surface of the associated notch (see FIG. 8C). However, once the top housing section 20 has reached the partially open position of FIG. 8B, a small amount of further movement in direction Z will cause the top housing section 20 to quickly move to the fully open position shown in FIG. 8A as pivot pin 39 will rotate due to gravity until the second flat section 134 of the outer wall 131 of the pivot pin 39 rests on a bottom flat surface 137 of the notch 86.

Likewise, the configuration of the outer wall of the pivot pins 39, 41 of the arms 38, 40 of the hinge bracket 36 provides an advantageous hinging action when closing the top housing section 20. When a user first begins to close the top housing section 20, the user must overcome the tendency of the pivot pins 39, 41 to return to the fully open position where the second flat section of the outer wall of the pivot pin rests on a bottom flat surface of the associated notch (see FIG. 8A). However, once the top housing section 20 has reached the partially open position of FIG. 8B, a small amount of further movement in direction Y will cause the top housing section 20 to quickly move to the closed position shown in FIG. 8C as pivot pin 39 will rotate due to gravity until the first flat section 133 of the outer wall 131 of the pivot pin 39 rests on a bottom flat surface 137 of the notch 86.

Regarding component construction, the top housing section 20, slide cover 28, hinge bracket 36, support structure 45 of the refill unit 44, frame 50, fan 60, chassis 80, battery door 96, bottom cover 102, and clip 110 may be formed from a suitable polymeric material such as polyethylene, polypropylene, or polyester.

In operation, the wearable chemical dispenser 18 will be clipped on a belt, purse or the like using clip 110 for that purpose. When a user moves the on-off button 29 along the side wall 22 of the top housing section 20 into the 'on' position, the openings 31 of the slide cover 28 align with the apertures 24 that are radially arranged in the top wall 23 of the top housing section 20. The cam projection 32 of the slide cover 28 is driven into the rotating activation button 56 which then contacts the microswitch 75 to turn on the power supply to power the fan 60 by way of motor 93. Air is sucked by the fan 60 of the wearable chemical dispenser 18 in through apertures 24 and the openings 31. As the air passes through fabric substrate 48, the air treatment chemical mixes into the air and a mixture of air and air treatment chemical is then blown radially out openings 91 (preferably down along pants or dresses). A user can rotate the clip 110 as described above.

While the present device is primarily intended to be used as a wearable item carried with a human when outdoors, it can also be laid flat, with the clip 110 downward and the top housing section 20 upward, on a picnic table or the like. When used in this manner it can provide protection to an area during a picnic or similar outdoor activity.

Hence, the device is much more compact and lightweight, yet still effective. Further, the cost of operation from a battery standpoint is reduced. The device can more comfortably be used when seated, and provides greater control over dispensing direction. Also, installing a replacement active refill is easier. These advantages are achieved at lowered cost, and provide a reliable construction.

In the wearable dispenser, the intake grill size is designed to work in concert with an improved fan which falls within a specific range of fan blades, size and blade angle. A low current draw motor is recessed into the axial hub of the fan design. The airflow exits through 270 of output vents. This combination of design features results in an ideal balance of airflow and minimal power consumption that results in a highly efficient system, which produces good insect repellency and usage duration in a relatively small, lightweight unit.

While an example embodiment has been described above, it should be appreciated that there are numerous other embodiments of the invention within the spirit and scope of this disclosure. For example, the device can be powered by a different source of energy (e.g. a solar power panel), other forms of actives can be dispensed along with or in substitution for the insect control ingredients (e.g. a fragrance or deodorizing chemical), and even when an insect control ingredient is dispensed it need not be one focused on controlling mosquitoes (e.g. chemicals for repelling other flying or crawling insects or pests can be used). Hence, the invention is not to be limited to just the specific embodiments shown or described.

INDUSTRIAL APPLICABILITY

Provided herein are wearable dispensing devices capable of dispensing insect control chemicals and/or other air treatment chemicals adjacent a human body.

What is claimed is:
1. A wearable device for dispensing an air treatment chemical, the device comprising:
 a housing including a top wall, an opposing bottom wall, and a side wall, the top wall of the housing defining an inlet for permitting air to enter into an interior space of the housing and including an outlet for permitting air mixed with air treatment chemical to exit the interior space, the side wall defining a perimeter of the housing;
 a fabric substrate positioned in the housing, the fabric substrate bearing an air treatment chemical;
 a power supply mounted to the housing;
 a motor mounted in the housing, the motor being powered by the power supply;
 a fan connected to the motor, the fan configured to draw air from the inlet through the fabric substrate so as to mix air treatment chemical into the moving air, and then deliver a mixture of air and air treatment chemical through the outlet to outside of the housing; and
 a clip including a front section spaced apart from a rear section, wherein the clip is rotatably connected to the bottom wall of the housing by the rear section, wherein the rotation of the clip is in a plane parallel to the bottom wall of the housing, and wherein an axis of rotation of the clip is positioned within the perimeter of the housing, wherein the clip is positionable in at least a first position, a second position, and a third position, wherein the second position is rotated 180 degrees relative to the first position and the third position is rotated 90 degrees relative to the first position and the second position, wherein the device further includes a visual use-up indicator that is viewable through a slot in the top wall, wherein the clip further includes an upper end and an opposing lower end that is configured to be flexed apart by a user, when the clip is in the third position, the upper end is positioned on an opposite side of the housing from a visual use-up indicator.

2. The device of claim 1 wherein the clip can rotate at least 90 degrees.

3. The device of claim 1 wherein the clip can rotate 180 degrees.

4. The device of claim 1 further comprising means for indexed rotational positioning of the housing and the clip relative to each other.

5. The device of claim 1 further comprising a detent system where there is a flexible tab on one of the clip and housing, and a series of distinct rest positions for the tab on another of the clip and housing.

6. The device of claim 5, wherein each such rest position is in the form of a depression, and the tab has a projection thereon.

7. The device of claim 1, wherein the front section of the clip is spaced apart from the rear section of the clip by a u-shaped top section.

8. The device of claim 1, wherein the bottom wall includes a battery cover, and wherein the clip is configured to rotate to provide access to the battery cover.

* * * * *